United States Patent
Redl et al.

(10) Patent No.: US 7,198,786 B2
(45) Date of Patent: Apr. 3, 2007

(54) METHOD FOR THE REDUCTION OR PREVENTION OF POST-SURGICAL ADHESION FORMATION

(75) Inventors: Heinz Redl, Vienna (AT); Reiner Spaethe, Starnberg (DE); Manuela Simunek, Vienna (AT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 373 days.

(21) Appl. No.: 10/399,223

(22) PCT Filed: Oct. 12, 2001

(86) PCT No.: PCT/US01/32044

§ 371 (c)(1),
(2), (4) Date: Jul. 23, 2003

(87) PCT Pub. No.: WO02/30446

PCT Pub. Date: Apr. 18, 2002

(65) Prior Publication Data

US 2004/0009917 A1    Jan. 15, 2004

(51) Int. Cl.
*A61K 38/00* (2006.01)
*A61K 38/48* (2006.01)

(52) U.S. Cl. ......................... 424/94.64; 514/2

(58) Field of Classification Search .................... None
See application file for complete search history.

(56) References Cited

FOREIGN PATENT DOCUMENTS

WO    99/56797    * 11/1999

OTHER PUBLICATIONS

Jahoda et al., "Fibrin sealant inhibits connective tissue deposition in a murine model of peritoneal adhesion formation", Surgery 125 (1) : 53-59 (1999).*
Lindenberg et al., "Prevention of peritoneal adhesion formation by fibrin sealant", Annales Chirurgiae et Gynaecologiae 73 : 11-13 (1984).*
Aliredjo et al., "The use of Gore-Tex membrane for adhesion prevention in tethered spinal cord surgery; Technical case reports", Neurosurgery 44 (3) : 674-678 (1999). abstract only.*

* cited by examiner

Primary Examiner—Sandra E. Saucier
(74) Attorney, Agent, or Firm—Townsend and Townsend and Crew LLP

(57) ABSTRACT

Reducing or preventing adhesions which would form in a patient during or after surgery by administering to the wound surface of a patient a fibrinogen solution in an amount of about 0.025 ml fibrinogen/$cm^2$ to about 0.25 ml fibrinogen/$cm^2$ of the surface being at risk for developing adhesions. User of fibrinogen in a preparation comprising fibrinogen at a concentration of 20 to 80 mg/ml for the reduction or prevention of post-surgical adhesion formation.

6 Claims, 1 Drawing Sheet

METHOD FOR THE REDUCTION OR PREVENTION OF POST-SURGICAL ADHESION FORMATION

BACKGROUND OF THE INVENTION

Post-surgical adhesions are a major healthcare problem of significant clinical and medical economic relevance. Abdominal adhesions are not only the leading cause of small bowel obstruction but also major sources of infertility and of abdominal and pelvic pain. It could be shown that post-surgical adhesions cause at least 20% of cases of infertility and about 40% of cases of chronic pelvic pain.

The great majority of adhesions in the Western world are induced by surgery. Although it is known that their incidence may be reduced by various improvements in surgical techniques and/or better instrumentation, adhesions cannot be prevented without adjuvant therapy, since every minute trauma may induce their formation.

Therefore, significant efforts have been made for providing effective means and treatment methods for reducing or preventing such adhesions connected with surgery. Many substances or constructs have been reported to have positive effects on surgical adhesions, such as collagen films, collagen gels, sodium hyaluronate/carboxymethylcellulose film and fibrin glue (see e.g. Arnold et al., Fertility and Sterility, 73 (1) (2000), 157–161).

Unfortunately, the process of adhesion and the factors influencing the criticality of such adhesions are largely still unknown. However, it is known that fibrinolysis appears to play a pivotal role in adhesiogenesis (c. Reviews of Holmdal and Holmdal et al. in Eur. J. Surg. (1997); Suppl.577:24–31 and 56–62).

The effect of the application of fibrinogen preparations or fibrin glues on anti-adhesion is highly controversial. Many earlier reports claim the possibility of prevention of the formation of postsurgical adhesions with such fibrin glues (e.g. Brands et al., Chirurg 61 (1990): 22–26; Lindenberg et al., Ann. Chir. Gynaecol. 73 (1984): 11–13; De Iaco et al., Fertility and Sterility 62 (2) (94): 400–404 and Takeuchi et al. (J. Am. Assoc. Gynecol. Laparosc. 3 (4) (1996): 575–579) or fibrinogen preparations, such as human cryoprecipitate (Toosie et al., The American Surgeon 66 (2000): 41–45; de Virgilio et al., Arch. Surg. Vol 125, October 1990, p. 1378 ff.)

However, other reports detected no significant effect of fibrin glues in preventing adhesion formation or enhancing reproductive outcome after adhesion complications during surgery (see e.g. Marana et al., Gynecol. Obstet. Invest. 41 (1996): 199–202 and Gauwerky et al., Arch. Gynecol. Obstet. 247 (1990): 161–166).

Recent research has concentrated on the development of barriers of fibrinolytic drugs and of selected agents, such as phospholipids. Comparative tests showed that resorbable barriers, such as collagen gels, collagen films and sodium hyaluronate/carboxymethylcellulose films, were effective in significantly reducing adhesion formation, whereas use of fibrin glues led to an incidence of adhesion formation similar to that in untreated control animals (see Arnold et al.; Holmdal (see supra)). These authors also demonstrated that the types of fibrinolytic inhibitors contained in all commercially available fibrin sealants significantly increased adhesion formation both to the parietal peritoneum and to the bowel compared with untreated control animals, whereas fibrinolytic activation with a recombinant tissue type plasminogen activator eliminated adhesion formation to the injured bowel and significantly reduced the number and extent of adhesions in the parietal peritoneum compared with untreated control animals.

It is therefore an object of the present invention to provide a suitable composition as well as a method for efficiently reducing or preventing post-surgical adhesions in a patient.

SUMMARY OF THE INVENTION

The present invention provides a method for reducing or preventing the formation of adhesions which would form in a patient during or after surgery, said method comprising administering to the wound surface of said patient a fibrinogen preparation in an amount of about 0.025 ml/cm$^2$ to 0.25 ml/cm$^2$ of the surface being at risk for developing adhesions.

The present invention also provides a fibrinogen preparation comprising, when in liquid form, 20 to 80 mg/ml fibrinogen for the efficient administration of fibrinogen in amounts effective for reducing or preventing post-surgical adhesion formation.

DETAILED DESCRIPTION OF THE INVENTION

Figure 1:
FIG. 1: Histological slide of mesothelium tissue repaired through use of the present invention.

The method according to the present invention is efficient in reducing or preventing adhesions in a patient by administering a fibrinogen solution in a specific amount, i.e. of about 0.025 ml/cm$^2$ to about 0.25 ml/cm$^2$ of a surface being at risk for developing adhesions. Surprisingly it was found that the administration of higher than 0.25 ml/cm$^2$ or lower than 0.025 ml/cm$^2$ does not result in an effective and reliable prevention or reduction of adhesions caused by surgery.

With amounts of fibrinogen solution lower than 0.025 ml per cm$^2$ surface the fibrin/fibrinogen layer provided seems to be too thin to provide an effective protection against adhesion formation. Amounts of fibrinogen higher than 0.25 ml/cm$^2$ surface yielded a layer with sufficient thickness but with very high clot persistance, i.e. the clot is not lysed within an appropriate time period. This high clot persistance leads to an inflammatory reaction on the surface which then leads to adhesion processes. Optimum amounts of fibrinogen solutions are around 0.1 ml/cm$^2$, e.g. between 0.07 to 0.13, especially 0.085 to 0.115 ml/cm$^2$. Optimally, a fibrinogen solution containing 35–55 mg/ml fibrinogen is used to administer these amounts to the wound surface.

For the method according to the present invention it is also critical that the fibrinogen solution be applied in a uniform mode, i.e. with a constant thickness over the whole surface area to be treated. Therefore, it is preferred to use a spraying device for the present invention. Suitable spraying devices are known in the art; preferred spraying devices are those known for the application of classical tissue adhesives. The application with needles is—although possible for a very skilled person—not generally recommended for the present invention. The fibrinogen preparation administered to the specific surface reacts with thrombin which is either added exogeneously together with the fibrinogen preparation (e.g. as a fibrin sealant kit) or with thrombin endogenously present in the patient at the administration site. The adhesions to be reduced or prevented with the method according to the present invention are those described in the prior art and may be adhesions to or between organs, parts of organs or tissues in a particular location. Generally adhesions may be defined as abnormal attachments between tissues and organs. Such attachments may be developed in response to trauma to the peritoneum. These trauma may be inflammatory or surgical and may include: exposure to infection or to intestinal contents, ischemia, initation from exogenous materials such as sutures, gauze particles or glove dusting powder, abrasion, desiccation or overheating by lamps or irrigation fluids.

The most relevant clinical adhesions are described as malformations or fibrinaceous glueings of peritoneum covered entrails which may lead to adhesion or briden ileus.

More specifically, such adhesions may occur after injury to or deformation of the peritoneum during surgery which may be caused e.g. by abdominal surgery, reproductive surgery, spinal surgery, laparatomy or other surgery in cardiac or abdominal procedures or in the gynecological area.

The patient may be human or any animal having a risk for or having such adhesions. The method according to the present invention may be useful for preventing and/or reducing newly formed adhesions as well as those adhesions which reform after adhesiolysis. Especially adhesions involving key organs and tissues, e.g. the small intestine or the uterus and adnexa, which are the most likely to be symptomatic, are treated or prevented.

In the method according to the present invention it is preferred to apply a thrombin preparation simultaneously with the fibrinogen preparation as known from the "classical" fibrinogen based tissue adhesives, as disclosed e.g. in the U.S. Pat. Nos. 4,298,598; 4,362,567; 4,377,572 and 4,414,976 as well as all the patents or applications citing these patents or their corresponding counterparts in other countries, which are incorporated herein by reference.

The thrombin preparation and the fibrinogen preparation may be provided as a set, preferably together with suitable administration devices, especially spraying devices, which are described in the EP 0 315 222 A, EP 0 156 098 A, EP 0 210 160 A and EP 0 292 472 A, which are incorporated herein by reference.

"Classical" tissue adhesives known in the art are provided in concentrations of at least 70–80 mg/ml fibrinogen. A physician of skill could practice the methods of the invention using fibrinogen preparations ranging from 20 to 150 mg fibrinogen/ml. However, for the purpose of reducing or preventing adhesions according to the present invention, a fibrinogen concentration of between 20 to 80 mg/ml, preferably 30 to 60 mg/ml, most preferably 35 to 55 mg/ml is preferred.

Commercially available fibrinogen preparations currently contain plasmin-acting fibrinolysis inhibitors such as aprotinin. Plasmin-acting fibrinolysis inhibitors should be omitted from the fibrinogen preparation to be used in the present invention. Non-plasmin-acting fibrinolysis inhibitors such as elastase inhibitors (WO 99/11301) can be included in the fibrinogen preparation for the practice of the present invention. Alternatively, fibrinolysis inhibitors can be omitted entirely from the fibrinogen preparation to be used in the present invention.

Preferably, the adhesions which are reduced or prevented according to the present invention are adhesions which would form during surgery such as gynecological or reproductive surgery, laparoscopic surgery or spinal surgery. In general, according to the present invention a reduction or prevention of adhesions which would be newly formed can be achieved as well as reduction or prevention of those adhesions which would reform after adhesiolysis, if the present invention were not used.

The fibrinogen preparation may contain Factor XIII and other other proteins such as fibronectin, which are known to be present in most commercially available fibrinogen preparations. The fibrinogen preparation may also contain additives such as antibiotics and cytokines.

The present invention provides an optimal preparation for administering fibrinogen to a wound site according to the method of the invention: the preparation of the invention comprises fibrinogen purified from a plasma pool, said fibrinogen, when in solution, being at a concentration of between 20 to 80 mg/ml, preferably 30 to 60 mg/ml, most preferably 35 to 55 mg/ml. Also provided is a set for the use in reducing or preventing post-surgical adhesions comprising the above described fibrinogen component together with a thrombin component.

According to a further aspect the present invention also relates to a method of repairing mesothelium damages comprising administering about 0.025 ml/cm$^2$ to about 0.25 ml/cm$^2$ of a fibrinogen solution to a damaged mesothelium.

Surprisingly, the administration of specific amounts of fibrinogen to a damaged mesothelium leads to a repair of the damaged tissue. Although it is known that fibrinogen solutions may inhibit peritoneal inflammation (Jahoda et al., Surgery 125(1) (1999), pages 53–59) it was never shown or proposed that such solutions may have a cell repair capability which allows a reliable and quick repair of a mesothelium being damaged in the course of surgical events.

The invention will now be explained in more detail by way of the following examples to which, however, it shall not be restricted.

EXAMPLES

1. Reduction and Prevention of Adhesion Using Different Amounts of Fibrinogen Preparations.

For the present test a fibrinogen containing preparation (40 mg/ml fibrinogen; 1–3 U/ml Factor XIII) was applied in different amounts (0.025 ml/cm$^2$, 0.05 ml/cm$^2$, 0.25 ml/cm$^2$) in a standard animal model for adhesions:

A modified rabbit model according to Rogers et al. (J. Invest. Surg. 9 (1996), 385–391 and J. Invest. Surg. 10 (1997), 31–36) was used for testing abdominal adhesion prevention involving formation of a peritoneal lesion and an additional defect in the cecum.

Rabbits are anesthetized and a median laparatomy is performed. The cecum is exposed and the upper side gently abraded with a gauze swab to induce de-epithelialization of the serosal surface of an approximately 30 cm$^2$ area until petechial bleeding occurs in the absence of muscle damage. Thereafter dynamic digital pressure is exerted to create subserosal hemorrhages over the surface of the cecum. In addition the lateral abdominal wall associated with the cecum position is pressed through a fixation frame causing protrusion of a 4.5×3 cm area of the parietal peritoneum. The externalized parietal wall is traumatized by removal of the peritoneum and the underlying transversal abdominal musculature.

To both lesions, test or control solutions in their predetermined volume are applied and the test solution is left to clot for 5 min. The distance of the delivery device from the surface of the tissue is around 10 cm. After 5 min both in the test group and control group the surface is wetted with 5 ml saline to prevent the area from drying up. The abdomen is closed. The muscle and skin incisions are sutured separately using Synthofil® 2/0 or Steelex 0/4 as interrupted sutures in a three-level manner.

For a period of 14 days, the animals are monitored daily for weight and clinical condition. at day 14, the animals are sacrificed and necropsies are performed to determine and quantify adhesion formation on the abdominal wall.

The adhesions are quantified by calibrated calipers. The area of attachment to the abdominal wall is calculated in mm$^2$ by multiplying the length and width of the adhesion attachment.

The results of the present tests are depicted in the following table 1.

TABLE 1

| Animal No. | Treatment | Surface area of Adhesion (mm$^2$) |
| --- | --- | --- |
| 1 | 0.025 ml/cm$^2$ | 0 |
| 2 | 0.025 ml/cm$^2$ | 0 |
| 3 | 0.025 ml/cm$^2$ | 24 |
| 4 | 0.025 ml/cm$^2$ | 837 |
| 5 | 0.025 ml/cm$^2$ | 0 |
| 6 | 0.025 ml/cm$^2$ | 0 |
| 7 | 0.025 ml/cm$^2$ | 0 |
| 8 | 0.025 ml/cm$^2$ | 600 |
| 9 | 0.025 ml/cm$^2$ | 0 |
| 10 | 0.025 ml/cm$^2$ | 44 |
| 11 | 0.05 ml/cm$^2$ | 0 |
| 12 | 0.05 ml/cm$^2$ | 7.5 |
| 13 | 0.05 ml/cm$^2$ | 0 |
| 14 | 0.05 ml/cm$^2$ | 0 |
| 15 | 0.05 ml/cm$^2$ | 0 |
| 16 | 0.05 ml/cm$^2$ | 63 |
| 17 | 0.05 ml/cm$^2$ | 0 |
| 18 | 0.05 ml/cm$^2$ | 0 |
| 19 | 0.05 ml/cm$^2$ | 0 |
| 20 | 0.05 ml/cm$^2$ | 0 |
| 21 | 0.25 ml/cm$^2$ | 0 |
| 22 | 0.25 ml/cm$^2$ | 0 |
| 23 | 0.25 ml/cm$^2$ | 0 |
| 24 | 0.25 ml/cm$^2$ | 0 |
| 25 | 0.25 ml/cm$^2$ | 221 |
| 26 | 0.25 ml/cm$^2$ | 0 |
| 27 | 0.25 ml/cm$^2$ | 0 |
| 28 | 0.25 ml/cm$^2$ | 0 |
| 29 | 0.25 ml/cm$^2$ | 1974 |
| 30 | 0.25 ml/cm$^2$ | 1750 |
| 31 | No fg | 1080 |
| 32 | No fg | 450 |
| 33 | No fg | 1400 |
| 34 | No fg | 672 |
| 35 | No fg | 1350 |
| 36 | No fg | 0 |
| 37 | No fg | 1560 |
| 38 | No fg | 1140 |
| 39 | No fg | 1980 |
| 40 | No fg | 1575 | no fg = control animals not treated with fibrinogen solution

Almost no adhesions have been observed with animals treated with tranexamic acid containing fibrinogen solution (Median=0), whereas for the animals treated with 0.025 ml/cm$^2$ or with 0.25 ml/cm$^2$ already a reduced preventive effect is observed, although the median surface areas effected by adhesion are still=0.

Control animals show a median of 1245 mm$^2$.

This indicates that the amounts of 0.025 and 0.25 ml/cm$^2$—although still performing well— are already outside the absolute optimum region for the present invention. The optimum amounts for the method according to the present invention are around 0.1 ml/cm$^2$, i.e. from about 0.07 to 0.13, also slightly depending on the fibrinogen concentration and potentially present non-plasmin-acting inhibitors of lysis. Higher fibrinogen concentrations and presence of inhibitors may shift the optimum towards lower values.

2. Mesothelium Repair

The efficacy of fibrin sealant for mesothelium repair after a lesion, which was induced as described in example 1, is shown in FIG. 1. After a certain time period the repair process is completed and a compact mesothelial layer has been formed on the damaged tissue surface.

We claim:

1. A method for reducing or preventing adhesions which would form in a human patient during or after surgery comprising administering to the wound surface of said patient a 20–80 mg/ml fibrinogen solution in an amount of about 0.025 ml fibrinogen/cm$^2$ to about 0.25 ml fibrinogen/cm$^2$ of the surface being at risk for developing adhesions.

2. A method according to claim 1 wherein said surgery is abdominal surgery.

3. A method according to claim 1 wherein said surgery is gynecological or reproductive surgery.

4. A method according to claim 1 wherein said surgery is laparoscopic surgery.

5. A method according to claim 1 wherein said surgery is spinal surgery.

6. A method according to claim 1 wherein said adhesions to be reduced or prevented would be newly formed adhesions or adhesions formed after adhesiolysis.

* * * * *